United States Patent [19]

Parton et al.

[11] Patent Number: 5,653,859
[45] Date of Patent: Aug. 5, 1997

[54] METHODS OF ANALYSIS/SEPARATION

[76] Inventors: Adrian Parton, 6 Swan Grove, Exning, Suffolk CB8 7HX, United Kingdom; Ying Huang; Xiao-Bo Wang, both of P.O. Box 89, Houston, Tex. 77030; Ronald Pethig, Lleyn, Telford Road, Mania Bridge, Gwynedd LL59 5DT, United Kingdom; Alastair R. MacGregor, Field House, Thriplow Road, Fowlmere, Royston, Hertfordshire SG8 7OT, United Kingdom; Denise V. Pollard-Knight, 20 Highfield Hall, Highfield Lane, St. Albans AL4 ORL, United Kingdom

[21] Appl. No.: 495,447
[22] PCT Filed: Jan. 21, 1994
[86] PCT No.: PCT/GB94/00121
§ 371 Date: Nov. 20, 1995
§ 102(e) Date: Nov. 20, 1995
[87] PCT Pub. No.: WO94/16821
PCT Pub. Date: Aug. 4, 1994

[30] Foreign Application Priority Data

Jan. 21, 1993 [GB] United Kingdom .................. 9301122

[51] Int. Cl.$^6$ .................. G01N 27/26; G01N 27/447
[52] U.S. Cl. .................. 204/450; 204/600
[58] Field of Search .................. 204/600, 450, 204/451, 452, 453, 454, 455, 602, 601, 603, 604, 605

[56] References Cited

U.S. PATENT DOCUMENTS

| | | | |
|---|---|---|---|
| 4,390,403 | 6/1983 | Batchelder | 204/457 |
| 4,900,414 | 2/1990 | Sibalis | 204/457 |
| 5,108,568 | 4/1992 | Van Alstine | 204/450 |
| 5,228,960 | 7/1993 | Liu et al. | 204/451 |
| 5,284,558 | 2/1994 | Linhardt et al. | 204/451 |
| 5,431,793 | 7/1995 | Wang et al. | 204/452 |

FOREIGN PATENT DOCUMENTS

| | | |
|---|---|---|
| 519250 | 12/1992 | European Pat. Off. . |
| 412745 | 2/1993 | Germany . |
| 92/07657 | 5/1992 | WIPO . |
| WO93/04199 | 3/1993 | WIPO . |

OTHER PUBLICATIONS

Senichi Masuda et al, "Separation of Small Particles in Liquid by Nonuniform Traveling Field", IEEE Transactions on Industry Appln. vol. A-23 No. 3 (May/Jun. 1987) 424-480.

Rolf Hagedorn et al, "Traveling-Wave Dielectrophoresis of Microparticles," Electrophoresis 1992 vol. 13 (1992) 49-54 No Month Available.

Masao Wastlizu, "Electrostatic Manipulation of Biological Objects", Journal of Electrostatics vol. 25, No. 1 (Jun. 1990) 109-123.

(List continued on next page.)

*Primary Examiner*—Kathryn L. Gorgos
*Assistant Examiner*—John S. Starsiak, Jr.
*Attorney, Agent, or Firm*—Cushman, Darby & Cushman IP Group of Pillsbury Madison & Sutro LLP

[57] ABSTRACT

Particles are subjected to travelling wave field migration (TWFM) to migrate the particles over an array of microelectrodes. Altered particles are produced by treating original particles in such a way so as to alter their TWFM characteristics and the altered TWFM characteristics are employed for analysis and/or separation of the altered particles. The particles may be cells, bacteria, viruses, biomolecules or plastics microspheres. They may be altered by binding to a ligand such as a metal microparticle via a selective linking moiety such as an antibody/antigen or oligonucleic acid, or be physical or chemical treatments.

14 Claims, 9 Drawing Sheets

OTHER PUBLICATIONS

Senichi Masuda et al, "Separation of Small Particles Suspened in Liquid by Nonuniform Traveling Field", IEEE Transactions on Industry Appln. vol. A–23 No. 3 May/Jun. 1987 pp. 474–480.

J.A.R. Price et al, "Applications of a new optical technique for measuring the dielectrophoretic behaviour if micro–organisms", Biochimica et Biophysica Acta vol. 964 (1988) pp. 221–230 No month available.

Rolf Hagedorn et al, "Traveling–wave dielectrophoresis of microparticles", Electrophoresis 1992 vol. 13 pp. 49–54 No month available.

W.D. Geoghegan et al, "The Detection of Human B Lymphocytes by both Light and Electron Microscopy Utilizing Colloidal Gold Labeled Anti–Immunoglobulin", Immunological Communications, vol. 7(1), pp. 1–12 (1978) No month available.

Y. Huang et al, "Electrokinetic behaviour of colloidal particles in traveling electric fields: studies using yeast cells", J. Phys D: Appl. Phys 26 (1993) pp. 1528–1535 No month available.

Masao Washizu, "Electrostatic manipulation of biological objects", Journal of Electrostatics 25 (1990) Jun., No. 1 pp. 109–123.

Journal of Electrostatics vol. 25, No. 1, Jun. 1990, pp. 109–123 M. Washizu, see p. 117, para 2; fig. 6,—see p. 120, para 4; p. 121, para 1.

IEEE Transactions on Industry Applications, vol. IA–23, No. 3, May 1987, pp. 474–480 S.Masuda: cited in the application—see the whole document.

Journal of Physics D. Applied Physics, vol. 26, Sep. 14, 1993, pp. 1528–1535, Y. Huang et al: cilted in the application, see p. 1534, col 2, para 2.

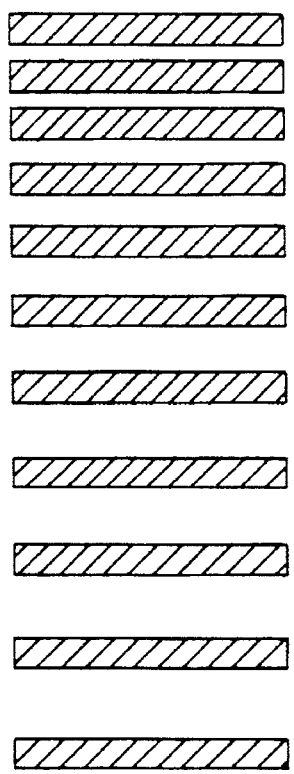 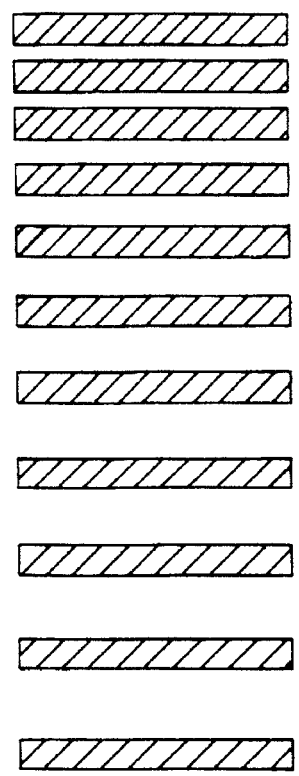
Figure 3
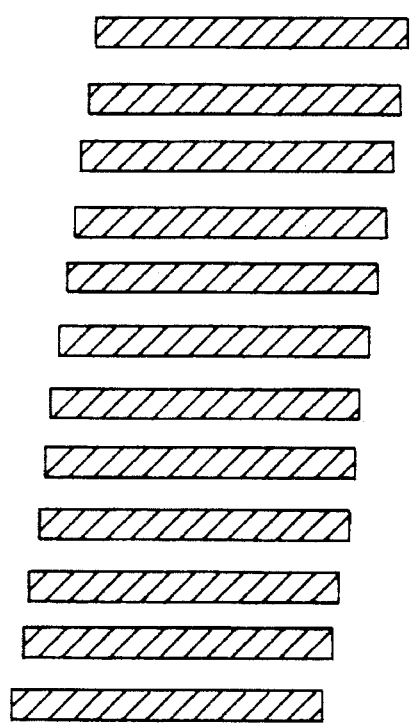 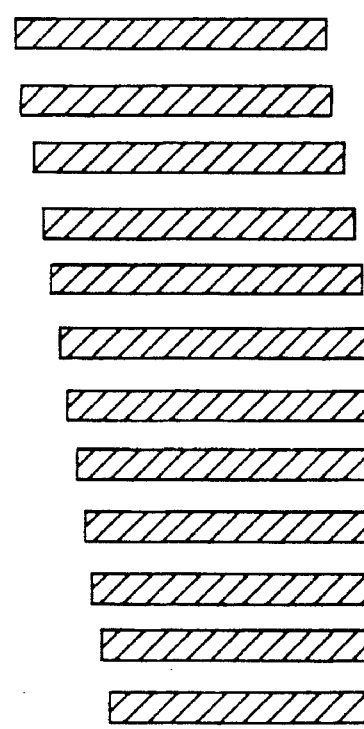
Figure 4

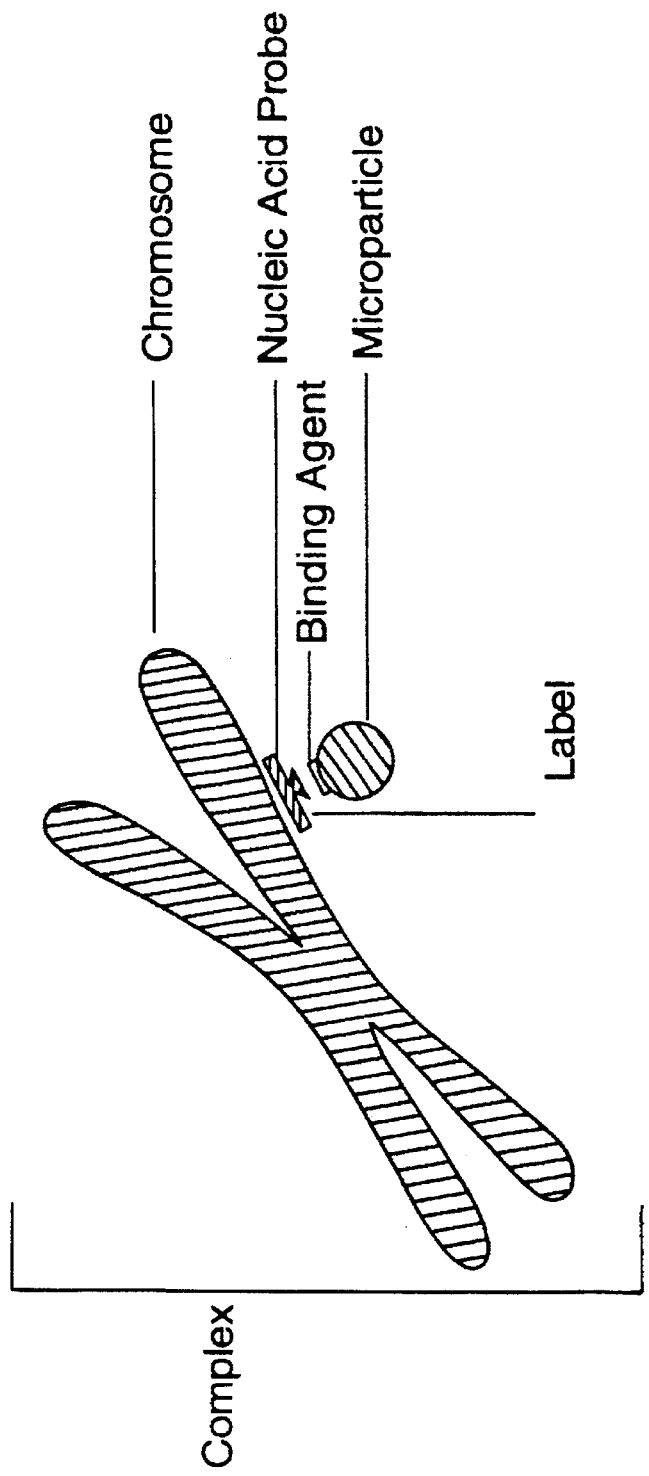
Figure 12 (not to scale)

"Polynomial" electrodes

METHODS OF ANALYSIS/SEPARATION

FIELD OF THE INVENTION

The present invention relates to analytical methods based upon the observation of the migration of particles in response to an electric field.

BACKGROUND OF THE INVENTION

By way of background, particles can be manipulated by subjecting them to travelling electric fields. Such travelling fields are produced by applying appropriate voltages to microelectrode arrays of suitable design. The microelectrodes have the geometrical form of parallel bars, which may be interrupted by spaces to form channels, as shown in FIG. 1 and may be fabricated using standard metal sputtering and photolithographic techniques as described by Price, Butt and Pethig, *Biochemica et Biophysica*, Vol.964, pp.221–230. Travelling electric fields are generated by applying voltages of suitable frequency and phases to the electrodes as described in a paper, title "Separation of small particles suspended in liquid by nonuniform travelling field", by Masuda, Washizu and Iwadare, IEEE Transactions on Industry Applications, Vol. IA-23, pp.474–480. Masuda and his coworkers describe how a series of parallel electrodes (with no channels) supporting a travelling electric field can, in principle, be used to separate particles according to their electrical charge and size (weight). Masuda et al have not however described a practical demonstration of such a particle separation method.

In a paper entitled "Travelling-wave dielectrophoresis of microparticles" by Hagedorn, Fuhr, Müller and Gimsa (Electrophoresis, Vol.13, pp.49–54) a method is shown for moving dielectric particles, like living cells and artificial objects of microscopic dimensions, over microelectrode structures and in channels bounded by the electrodes. The travelling field was generated by applying voltages of the same frequency to each electrode, with a 90° phase shift between neighbouring electrodes.

In "Electrokinetic behaviour of colloidal particles in travelling electric fields: Studies using Yeast cells" by Y Huang, X-B Wang and R Pethig J. Phys. D. Appl. Phys. 26 1993 1528–1535, an analysis supported by experiment is made of the "travelling-wave dielectrophoresis" (TWD) effect described by Hagedorn et al (paper cited above). The phenomenological equation $$\mu = -\frac{2\pi\epsilon_m r^2}{3\lambda\eta} A^2(O) Im[f(\epsilon_p{}^*, \epsilon_m{}^*)]$$

is developed by Huang et al, to show that the TWD velocity is a function of the square of the particle radius (r), the square of the electric field strength (A(0)), the periodic length of the travelling field ($\lambda$), medium viscosity ($\eta$) and the imaginary part of the Clausius-Mossotti factor $f(\epsilon_p{}^*, \epsilon_m{}^*)$ defining the dielectric properties of the particle and the suspending medium in terms of their respective complex permittivities $\epsilon_p{}^*$ and $\epsilon_m{}^*$. This equation provides, for the first time, a practical guide for the design of travelling wave electrode systems for the manipulation and separation of particles.

Although the phenomenon in question is usually termed "travelling wave dielectrophoresis", we have now demonstrated that this is something of a misnomer as the force which acts on the particles to produce translational movement is not the dielectrophoresis force but rather that which acts in electrorotation. This force is related to the imaginary component of the polarizability of the particle within its surrounding medium. However, as is discussed in more detail below, particle migration only occurs for travelling wave frequencies which produce negative dielectrophoretic forces on the particle. (Dielectrophoretic forces are related to the real component of the polarizability of the particle within its surrounding medium.) These forces are responsible for lifting the particle away from the electrodes and the channel between the electrodes. We accordingly prefer to refer to the phenomenon called previously "travelling wave dielectrophoresis" by the name "travelling wave field migration" (TWFM). We have established that to obtain TWFM, two separate criteria have to be met. First, a frequency must be selected at which the dielectrophoresis force acting on the particles is negative, i.e. such as to repel the particles from the electrodes. This, we have found requires the real component of the dipole moment induced in the particles to be negative.

Second, the frequency selected has to be such that the imaginary component of the dipole moment induced in the particles is non-zero (whether positive or negative) to produce a force displacing the particles along the array of electrodes.

The present invention is based upon the observation that the TWFM characteristics of a particle (i.e. the direction and speed at which it moves under TWFM and the conditions including electrode layout and spacing, voltage, frequency and suspending medium under which TWFM is possible) can be altered by a selection of methods which affect the dielectric characteristics of the particle concerned.

The present invention provides a method of analysis or separation comprising treating a particle to form an altered particle, which altered particle has TWFM properties distinct from those of the original particle, and producing translational movement of the altered particle by TWFM using conditions under which the movement of the altered particle is different from that which would be obtained using the original particle under identical conditions.

The particle may be of a size to be visible using a light microscope (a microscopic particle) or may be smaller (a sub-microscopic particle) and may be detected using labels such as luminescent, fluorescent and electromagnetic radiation absorbent labels.

Examples of the former type of particles include mammalian cells, plant cells, yeast cells, plastics microbeads, chromosomes undergoing meiosis and mitosis and oocytes, e.g. of Cryptosporidium.

Examples of the second type would include bacterial cells, viruses, DNA or RNA molecules, proteins, other biomolecules, and chromosomes.

The nature of the treatment used to convert the original particle into an altered particle can vary widely according to the nature of the particle. The treatment may involve forming a complex between the particle and a ligand. In some cases, the complex may involve a linking moiety connecting the particle and the ligand. The complex may further include a label connected to the ligand, optionally via a second linking moiety. The complex may involve numerous ligands bound to the particle.

The choice of linking moiety will obviously depend on the nature of the particle and the ligand. For instance if one wishes to capture a nucleic acid species (the ligand) on a plastics micro-sphere (the particle), the linking moiety will normally be chosen to be a nucleic acid or nucleic acid analogue oligomer having a sequence complementary to that of the ligand or a part thereof.

The linking moiety may be bound first to the particle and may then be a species having an affinity for the ligand.

Preferably, the affinity for the ligand is a selective affinity such that the formation of the complex between the particle and the ligand is selective and provides at least a degree of identification of the ligand. Preferably, the affinity is highly specific and accordingly the linking moiety bound to the particle which provides the selective affinity for the ligand may be an antibody or an antibody fragment having antibody activity, an antigen, a nucleic acid probe or a nucleic acid analogue probe having selective affinity for complementary nucleic acid sequences, or avidin or an avidin-like molecule such as strept-avidin.

Antibodies and antibody fragments having antibody properties are particularly preferred. There are known techniques suitable for coating antibodies on to the surface of particles such as plastics micro-beads which are well known to those skilled in the art. Antibody coated particles are capable of recognizing and binding corresponding antigens which may be presented on micro-organism cells or some other ligand.

Methods are also known for binding oligo-nucleic acid probes to such micro-beads. Suitable techniques are by way of example described in PCT Application No. GB92/01526, which was published Mar. 4, 1993 under No. WO 93/04199. Where the linking moiety is a nucleic acid probe or a nucleic acid analogue probe, the resulting particle will of course be suitable for recognizing and binding complementary nucleic acid sequences.

The ligand may be chosen to increase the visibility of the particle or otherwise improve its detectability as well as to alter its TWFM characteristics. For instance antibodies bearing fluorophores or chromaphores may be bound to the particle so that the complex so formed can be distinguished from the starting particle by TWFM and detected by fluorescence or colour.

The label may be bound to the ligand either before, simultaneously with, or after the formation of the complex between the ligand and the particle. The label may comprise a second linking moiety carried by the label. Once again, it is preferred that the affinity for the ligand possessed by the second linking moiety is selective, preferably highly specific and the second linking moiety may also be an antibody, an antibody fragment having antibody activity, an antigen, a nucleic acid probe, a nucleic acid analogue probe, avidin or an avidin-like molecule. The use of a label of this nature may be desired to aid ready detection of the complex and/or where a complex between the particle and the ligand does not in itself possess sufficiently distinctive TWFM properties, thus the TWFM may be further altered by the inclusion in the complex of the label. To this end, the label may be a fluorophore or chromaphore, or a micro-organism, a metal particle, a polymer bead or a magnetic particle. For use in connection with TWFM measurements, the label preferably has dielectric properties and is capable of acquiring a significant surface charge. A particularly preferred material is colloidal gold which is easily bound to antibodies (as the second species) to form a label. Antibodies bound to colloidal gold are commercially available and methods for binding antibodies to colloidal gold are for instance described in Geohegan W. D. et al (1978) Immunol. Comm 7 pl. Other metal particles however may be employed, e.g. silver particles and iron particles.

The use of a label of the kind described above may be preferred even where a complex between the ligand and a particle possesses sufficiently distinctive TWFM properties to enable the formation of such a complex to be observed. A higher level of specificity may in certain cases be obtained by the use of a label in such a complex. Thus for instance, one may wish to distinguish a micro-organism expressing an antigen A from a micro-organism expressing antigens A and B. This may be accomplished by the use of micro-particles having as a linking moiety an antibody to A and a label having as it's moiety an antibody to B. The difference in the velocities of the labelled complex (between the micro-particle, the micro-organism and the label) and the unlabelled complex (between the micro-particle and the micro-organism) can be observed, and used to distinguish micro-organisms expressing antigen A only, from those expressing A and B.

The label may include a magnetic particle so that the label can be attracted to a magnet so as to concentrate complexes containing the label for easier observation. In some cases it may be possible to attract labelled complexes to a magnet and to wash away unlabelled particles so as to eliminate the background of particles bearing linking moieties but no ligand/label, which would normally be present. Suitable magnetic labels for this purpose will include iron micro-particles bearing linking moieties such as antibodies. Such antibody coated iron particles are commercially available.

Labels for both cells and smaller particles can include fluorescent markers, e.g. FITC or rhodamine, chromophores, luminescent markers or enzyme molecules which can generate a detectable signal. Examples of the latter include luciferases and alkaline phosphatase. These markers may be detected using spectroscopic techniques well known to those skilled in the art. The label could be bound to the ligand either before, simultaneously with, or after the formation of the complex between the ligand and the particle. In the case of cell transfection, the cells may co-express a marker with the gene product. For example, the gene for firefly or bacterial luciferase may be co-transfected into the cells enabling the transfected cells to be visualized by a luminescent signal.

The alteration of the original particle need not involve the formation of a complex. For instance, the TWFM characteristics of a cell may be altered by heating or by treatment with a reagent which alters the porosity of the cell membrane. Accordingly, the alteration may be in the particle itself rather than or in addition to a change due to the physical presence of a ligand in a complex. Both effects may be present in combination. A ligand forming a complex with a particle may exert a physical effect on the TWFM properties and also by interaction with the particle bring about a change in the intrinsic TWFM properties of the particle.

The invention includes methods as described above carried out for analytical purposes and also such methods carried out for preparative or other purposes.

The methods according to the invention may be employed in a wide variety of analytical applications including separation and analysis of samples containing cells for example, bacterial, mammalian, yeast, and insect cells or virus particles, and, biological macromolecules. Current methods of separating cells, for example flow cell cytometry, require expensive instrumentation, skilled operators and significant laboratory resources. The techniques also have limitations when there are many different cell populations to be separated and when the cells of interest represent less than a few percent of the total. For separation and analysis of modified biological molecules, or complexes between biological macromolecules, employed techniques include electrophoresis and chromatographic separation using gel-filtration or affinity chromatography. Although these, in some cases, provide adequate separation, for many applications they can be time consuming and have limited resolution. In addition, use of these methods can affect the equilibrium between biological complexes. For example, gel-filtration results in a significant dilution of the sample.

Methods described hereafter according to the present invention allow some or all of these drawbacks to be addressed.

Where in an analytical method according to the invention a complex between the particle and a ligand is produced, the ligand need not itself be the species to establish the presence, nature or quantity of which is the ultimate purpose of the analysis. Thus, the ligand may be a reagent in the analysis and the species of interest in the analysis may be another component of the complex, e.g. the linking moiety or the particle itself. Where a particle is altered by treatment with a reagent, it may be the particle or the reagent which is essentially to be studied.

The process of TWFM described previously has been carried out using an array of linear, parallel electrodes subjected to phased electric fields normally such that every fourth electrode along the TWFM path is in phase. This periodicity defines the effective wave length of the travelling wave field produced. We have established that this wave length is optimally about ten times the average diameter of the particle to be moved under TWFM, e.g. from 5 to 20 times or more preferably 8 to 12 times said average diameter. For particles which are not roughly circular, it is the length in the direction transverse to TWFM movement which is of significance.

The electrodes may be formed, depending on the dimensions required, using any of the standard techniques for patterning and manufacturing microscopic structures. For example the electrodes can be produced by:

screen printing;

deposition of electrode material (e.g. by electroplating or sputter deposition) followed by one of the following patterning techniques:

direct writing using an electron beam followed by etching (e.g. wet chemical etching, dry plasma etching or focused ion beam etching);

writing by exposure through a photolithographically generated mask followed by etching—the mask may be generated for example by visible, ultra violet, X-ray or electron beam lithography;

excimer laser ablation;

patterning followed by deposition of the electrode material (as in the X-ray LIGA process).

BRIEF DESCRIPTION OF THE DRAWINGS

The invention will be further described and illustrated by the following description of apparatus and methodology with reference to the accompanying drawings in which:

FIG. 3 shows a modified electrode array in which the electrode spacing varies along the array.

FIG. 4 shows a further modified electrode array in which the electrode spacing varies across the array;

FIG. 12 shows a complex in which the particle is a chromosome constituting an altered particle for use in the invention;

BRIEF DESCRIPTION OF THE PRESENTLY PREFERRED EXEMPLARY EMBODIMENTS

Examples of electrode designs for achieving separation effects are shown in FIGS. 1 to 6.

Figure 1:
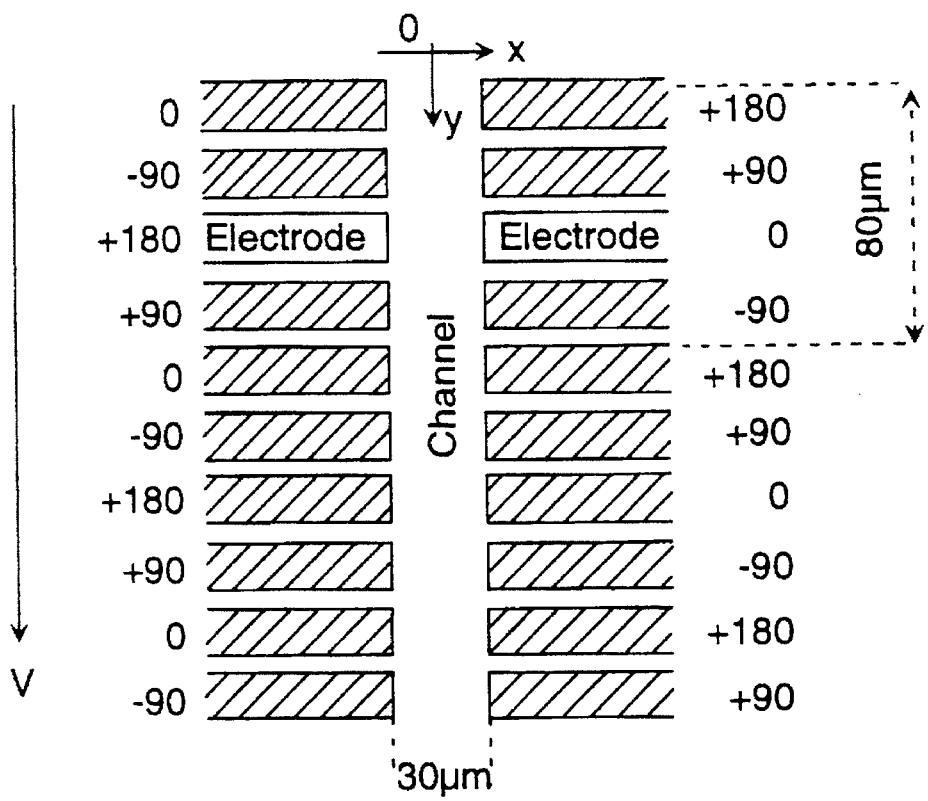
FIG. 1 shows an electrode layout and voltage phase relationships for use in producing TWFM.

In FIG. 1, the array of electrodes is constituted by two parallel rows of electrodes, each electrode being rectangular and elongate transverse to the direction of extension of the rows. The two rows are separated by a gap of constant width and the separation between each pair of electrodes in each row is the same. The electrodes are thin metal film electrodes on an insulating substrate, suitably gold electrodes printed on a glass slide. The separation between the rows is 30 μm and the pitch between groups of four electrodes in each row is 80 μm. A useful rule is that generally the said pitch defining the wave length of the travelling wave should be from 5 to 20 times the size of the particle, e.g. 8 to 12 times, most preferably 10 times.

Figure 2:
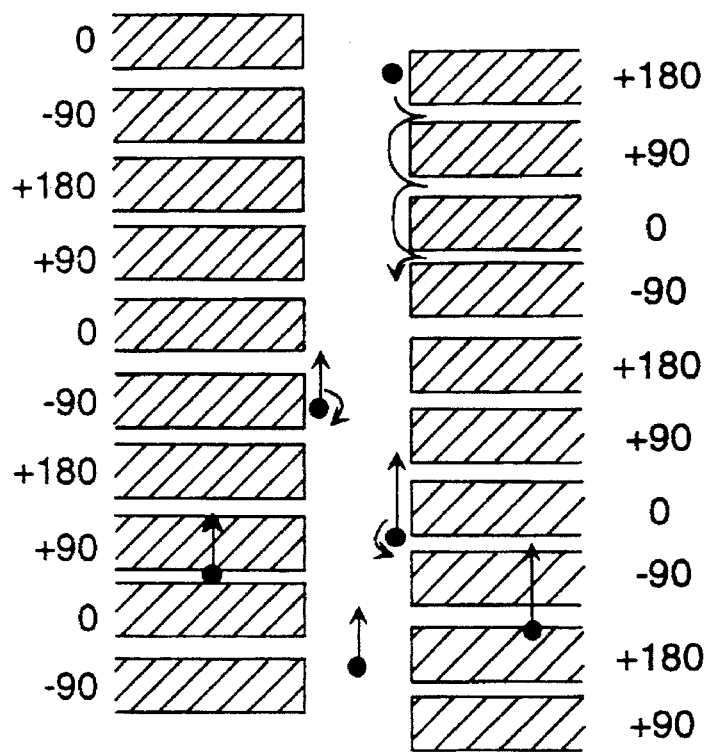
FIG. 2 shows the possible patterns of movement of particles over the electrode array shown in FIG. 1.

As shown in FIG. 2, the response of particles exposed to a travelling wave field of the kind described below can be varied. Particles can be collected on the electrodes, they can be induced to spin and they can be caused to travel along the gap between the rows or over the electrode rows. This last type of movement is TWFM. The type of motion produced depends upon the nature of the particle, the suspending medium, the electrode spacing and the field frequency.

In FIG. 3, the periodic length between electrodes varies, so as to bring into effect the parameter λ in the above equation. For example, a travelling wave moving from the top to bottom electrodes, will accelerate a particle moving upwards under TWFM. This may be used for example to produce more uniform resolution along the TWFM path, counteracting a natural tendency for resolution to increase with distance travelled. In FIG. 4 the channel width also varies, and this brings into play the variation of the field A(0) of the above equation. A particle moving under TWFM will be accelerated as a result of the field increasing as the channel width decreases. Thus, two particles of different size but otherwise similar physico-chemical properties will be spatially separated as they move along the channel. Particles of different dielectric properties could be suspended in suitable medium such that the factor Im[f($\epsilon_p^*, \epsilon_m^*$)] in the above equation has a different sign for each particle. The particles would then physically separate by moving in opposite directions under TWFM.

Figure 5:
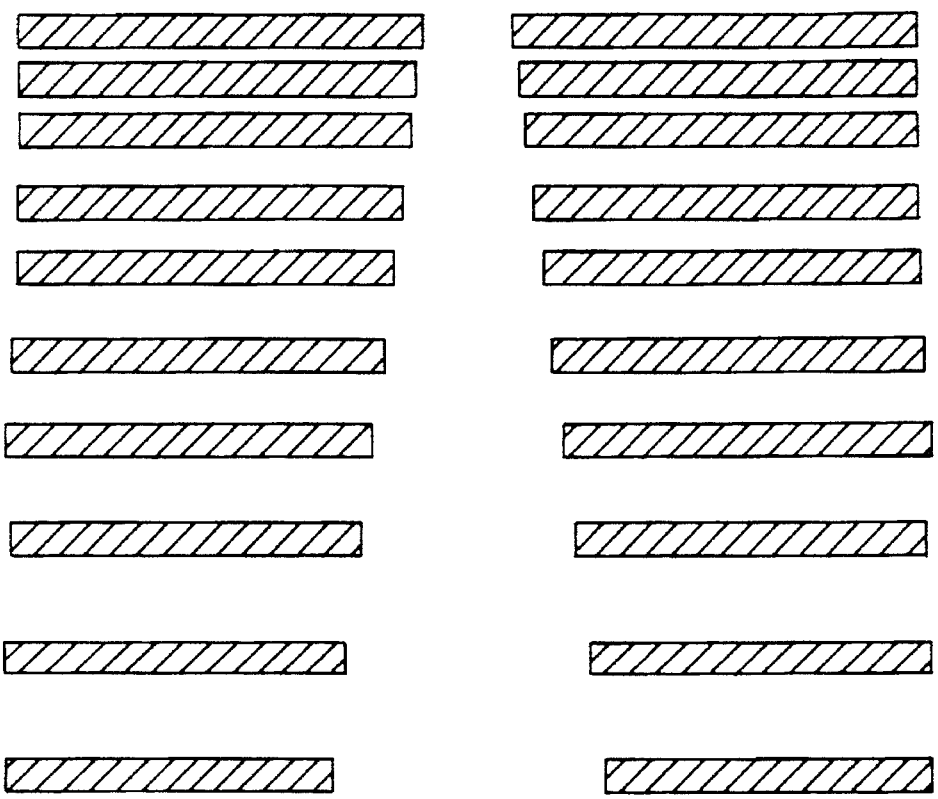
FIG. 5 shows a further modified electrode array in which the electrode spacing varies both across and along the array.
Figure 6:
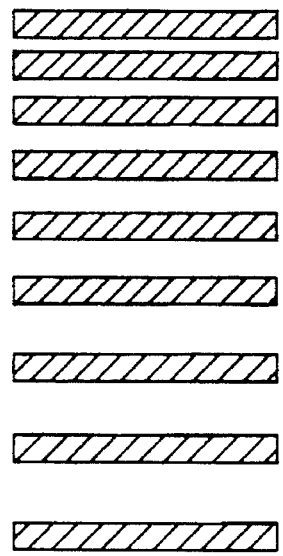
FIG. 6 shows an electrode array in which the central channel present in the arrays shown in earlier figures is absent.

FIG. 5 is an electrode design that combines the influence of λ and A(0). Particles can also be induced to move over parallel electrodes under the influence of travelling fields, and an example of an electrode geometry where separation can be achieved using differential particle acceleration is shown in FIG. 6.

The particles will move under TWFM unless they are trapped by positive dielectrophoresis forces (as described in the work of Huang et al). This provides an extra facility for selectively trapping and separating particles according to their dielectric properties and size.

Figure 7:
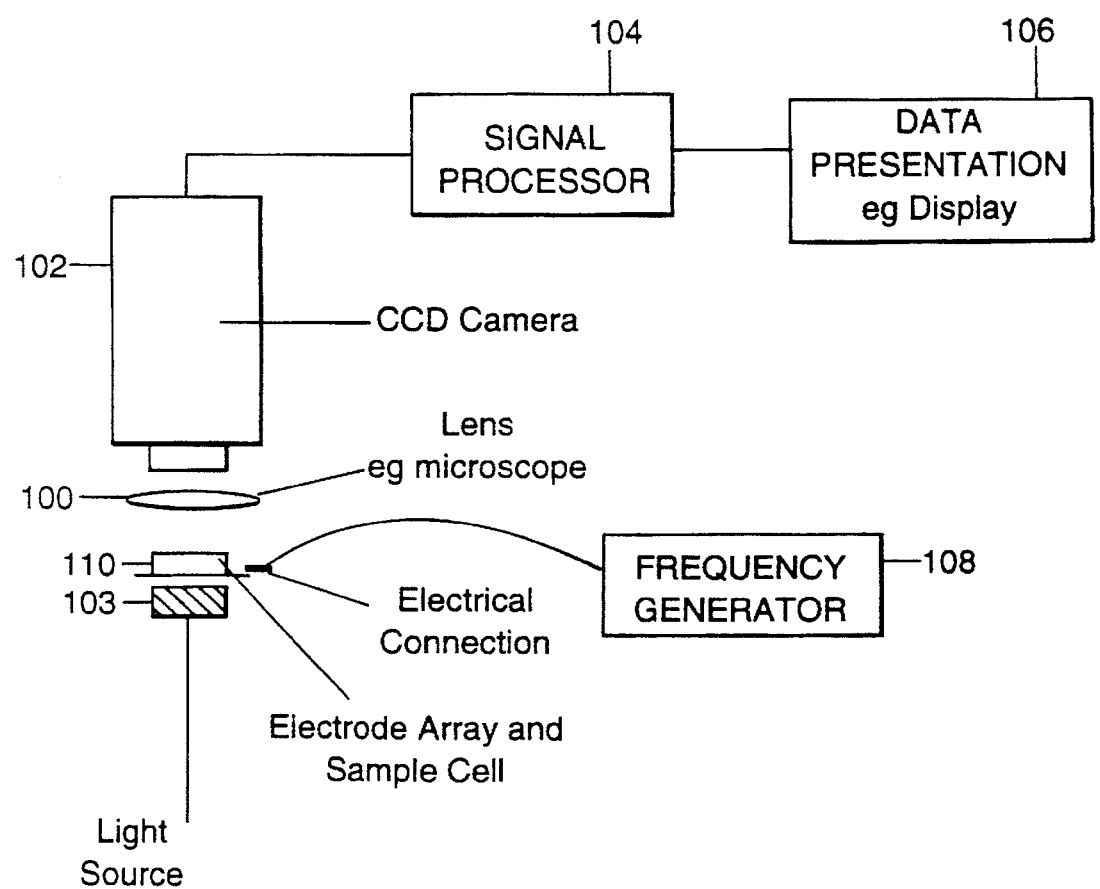
FIG. 7 shows schematically the components of apparatus for carrying out methods according to the invention and gathering data therefrom.

As shown in FIG. 7, apparatus for use in accordance with the invention comprises a light microscope schematically indicated by a lens 100 which is equipped with a CCD camera attachment 102 as well as a conventional field illuminating light source 103 and slide carrier stage (not shown).

The CCD camera 102 is connected to a signal processor unit 104 and to a display screen 106. The apparatus further comprises a frequency generator 108 which in use is connected to terminals provided on a microscope slide 110 which bears a pattern of electrodes as shown in more detail in FIG. 1.

The electrodes may be printed, e.g. in gold, or coated and etched on the microscope slide 110 together with tracks leading to terminals for connection to the frequency generator 108. The frequency generator provides the electrical field output. The frequency generator is provided with variable outputs to enable the operator to set the frequency of the sine wave outputs and the peak peak voltage of them.

In use, the image appearing on the display of the apparatus shows a number of beads within the field of the microscope migrating sufficiently slowly that the rate of migration within a period such as 30 seconds can be determined directly by an observer looking at each bead in Turn. Whilst apparatus described above is sufficient to produce useful results as demonstrated by the specific examples given below, it is generally preferable that migration speed measurements be carried out on more beads than a human observer could reasonably deal with directly. For this purpose, it will be desirable to use image processing techniques to detect and measure the migration of the beads in the apparatus. From the CCD camera attachment, one may derive images of a field of view containing a number of migration beads. A series of such images, or frames, may be captured by frames-grabber circuitry in a computer and the series of the images may be analyzed by image processing software.

Thus, a thresholding process may be used for example to convert the grey scale image produced by the camera into a binary image. A separate thresholding operation is performed to identify any areas of the image which are considered too dark, these areas being removed from the binary image of the beads. The remaining shapes in the image may be separated from the rest of the image and subjected to a test of one of more characteristic properties, such as area, to select those which are likely to represent beads. The centre of mass may then be determined for each qualifying shape. The positions of the centres may be compared between the successive frames in order that each bead in one frame may be located in the next. Once a bead has been located in two frames, the difference in the position of the bead will give directly the migration distance from which its migration rate may be calculated and averaged over several pairs of frames. By such automated techniques the migration speeds of all of the beads within the field of view at any moment may be measured and a statistical picture of the migration characteristics of the beads may be developed, optionally using a number of field migration frequencies.

Other image processing techniques may also be used to identify the position of particles and to determine their movement, for example correlation, edge detection, or morphological techniques or images subtraction. Neural networks may also be used to identify particles.

It is not always necessary to use an imaging detector of the type described above to determine particle velocities. Alternative detection configurations include:

light scatter detectors, as in a flow cytometer;

standard fluorescence detection arrangements;

luminescence detection using CCDs or other detectors;

single or multi-element optical spectroscopic measurements;

refractive index modulation detection (eg by phase contrast techniques);

detection by acoustic impedance measurement (which is related to particle mass) using surface or bulk acoustic sensors;

electrical impedance, capacitance, or inductance.

The apparatus may be further modified by the inclusion of a magnet, suitably an electro-magnet, positioned to draw any magnetic beads in the sample into the field of view of the microscope. The magnet would then be removed or turned off whilst the migration characteristics of the beads were measured. Alternatively, the particles may be manipulated into position by dielectrophoresis or electrophoresis.

Figure 8:
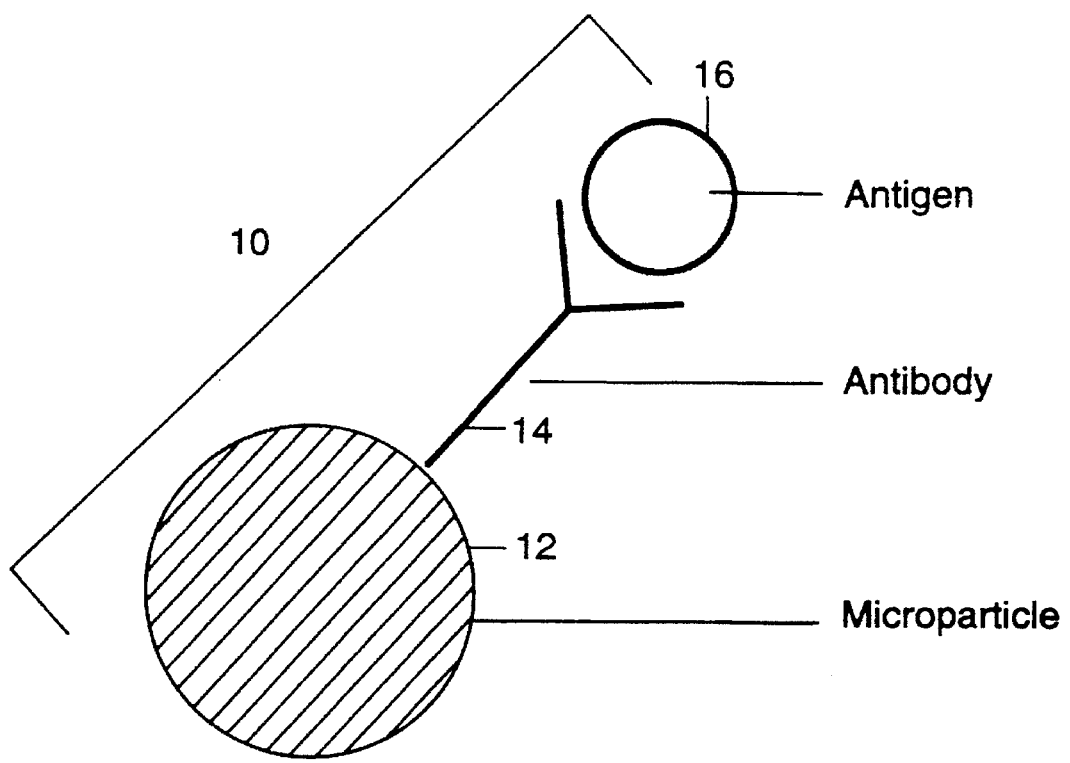
FIG. 8 shows schematically a complex constituting an altered particle used in an embodiment of the invention.

As shown in FIG. 8 a micro-particle may comprise a plastics bead 12 having bound to it as a linking moiety one or more antibody molecules 14. It should be noted that the drawing is not to scale and that normally in reality the plastics beads will be coated with a multitude of antibody molecules. The micro-particles may be exposed to micro-organism cells 16 bearing surface antigens reactive with the bound antibody to form a complex 10 between the micro-particle and the cell. The micro-organism cells may for instance be *E. coli* or *coliforms* present in water or pathogenic micro-organisms present in foodstuffs such as listeria or salmonella. It has been found that the rate of migration of such micro-particle/micro-organism cell complexes under suitably chosen conditions is distinguishable from the migration rates obtained using the micro-particles alone and furthermore that the migration rates obtained for complexes between micro-particles and viable micro-organism cells can be distinguished from those obtained between micro-particles and similar non-viable cells.

Figure 9:
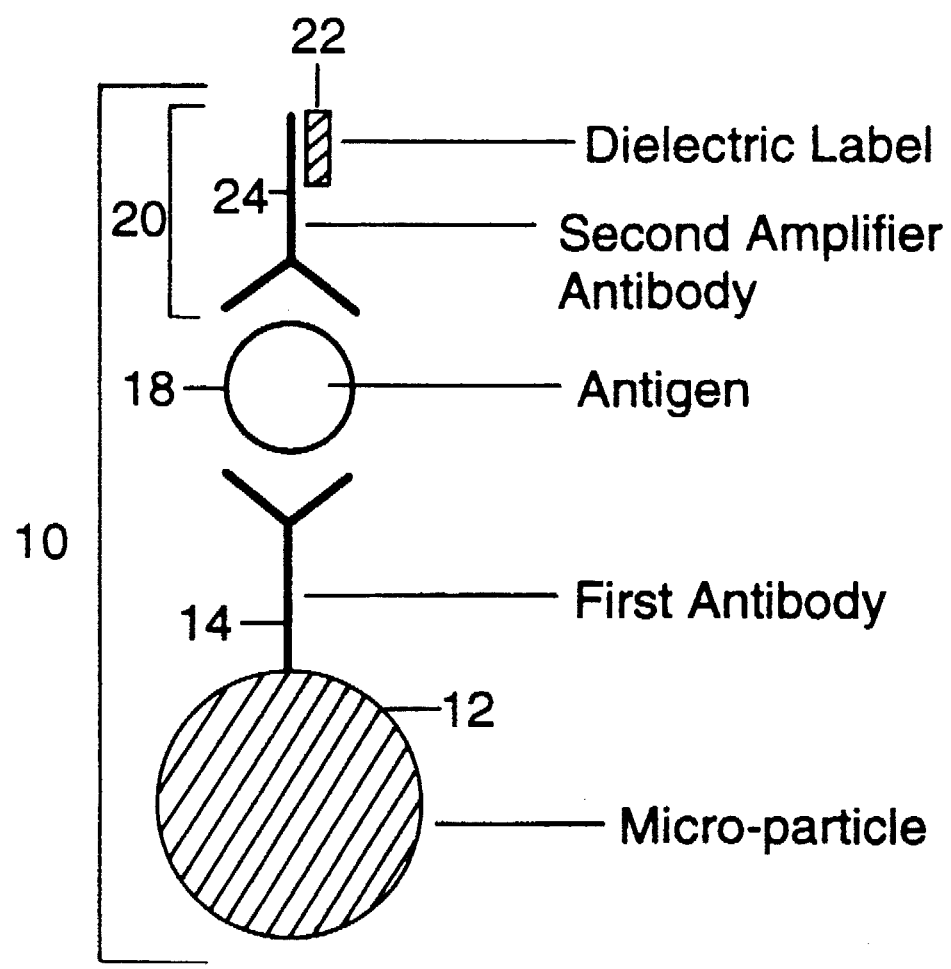
FIG. 9 shows schematically a ternary complex constituting an altered particle used in an embodiment of the invention.

As shown in FIG. 9, a ternary complex 10 may be produced between a micro-particle 12 of the kind shown in FIG. 8 as described above, an antigen 18 and a label 20 comprising a labelling moiety 22 and a second antibody 24 which may be the same as or different from the antibody 14. A ternary complex of this type may be employed where the antigen 18 is too small or lacking in dielectric properties sufficiently to affect the TWFM properties of the micro-particle 10 or where it is desired to obtain a higher level of specificity through the use of two different antibodies in a single analysis. The antigen may for instance be a toxin present as a contaminant in a foodstuff.

Figure 10:
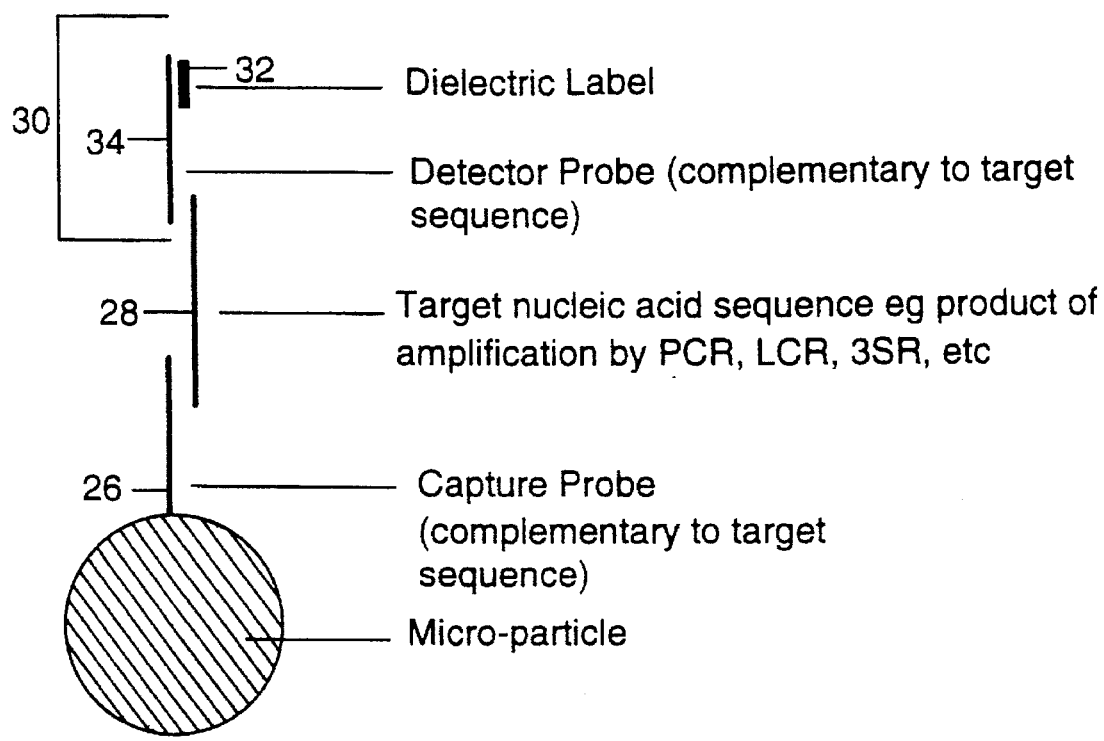
FIG. 10 shows a further ternary complex constituting an altered particle used in an embodiment of the invention.
Figure 11:
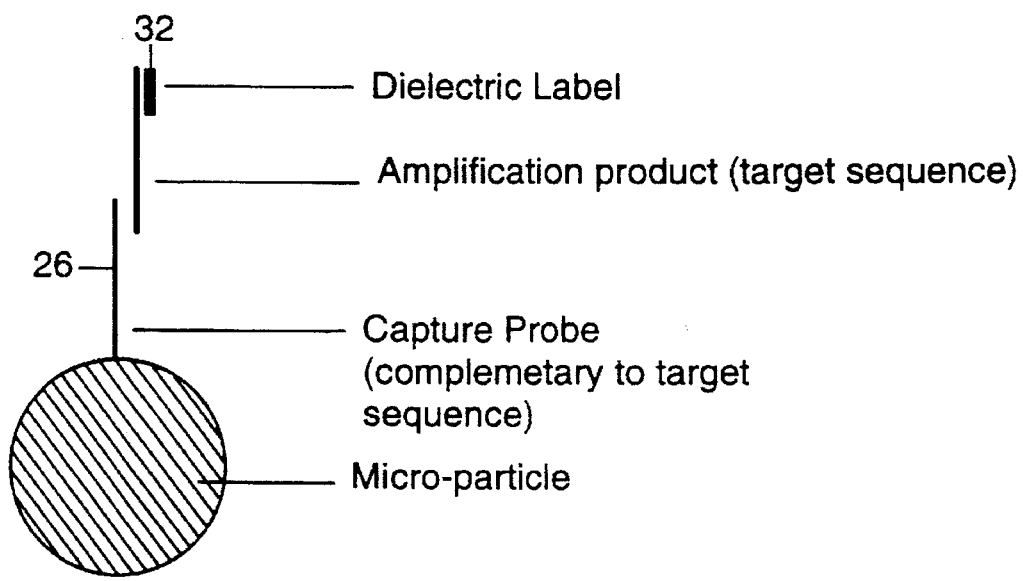
FIG. 11 shows a further binary complex constituting an altered particle used in an embodiment of the invention.

FIGS. 10 and 11 illustrate methods of detecting nucleic acids and in particular nucleic acid sequences produced as products of amplification procedures such as PCR, LCR and 3SR techniques. Known methods of detecting nucleic acid amplification procedure products rely upon them undergoing some form of purification and/or separation procedure before they are analysed. One commonly used method involves the analysis of the products by agarose gel electrophoresis. This separates the amplified DNA fragments and any remaining oligonucleotide primers on the basis of size. Separating products on the basis of size alone does not enable one to distinguish between PCR products of the required base sequence and an amplified contaminant of approximately the same length. In order to further identify PCR products, the gel electrophoresis may be taken one step further by subjecting its product to the Southern blotting technique in which the separated fragments are transferred from the gel to a membrane in direct correspondence to their relative positions on the gel. They are then probed with a labelled single stranded DNA probe with a base sequence complementary to the sequence of interest. The label used for the probe is usually biotin or a radio-isotope such as $^{32}p$. Southern blotting is relatively laborious and requires a moderate level of laboratory skill as well as laboratory equipment and facilities. It is not suited for use in rapid screening of a large number of samples or the screening of samples outside the laboratory. The method of dot blotting in which the agarose gel separation step of Southern blotting is omitted is somewhat quicker but basically suffers from the same disadvantages as Southern blotting.

As illustrated in FIG. 11, in a method according to the present invention a microparticle may include an oligonucleotide or synthetic oligonucleotide analogue as a capture probe 26 (linking moiety) bound to the surface of a polymer bead and having a sequence complementary to that of an expected amplification procedure product 28. A label 30 comprising an TWFM labelling moiety 32 as described above bound to a second oligonucleotide or oligonucleotide analogue sequence 34 complementary to a second region of the ligand nucleic acid sequence is employed. The micro-particles and the label may be added to the product of the amplification reaction before or after any working up of the reaction mixture to separate the amplification products. The TWFM properties of the micro-particle/amplification product/label ternary complex may then be observed and distinguished from those of the micro-particles alone. A variant on this procedure is illustrated in FIG. 8 in which one of the primers used in the amplification procedure is labelled with a suitable TWFM labelling moiety 32 which thereby becomes covalently incorporated into the nucleic acid product of the amplification procedure. A binary complex is then produced between a micro-particle bearing a capture probe 26 and the amplification product and the TWFM properties of the complex are observed.

In a variant of FIG. 11 shown in FIG. 12, the ligand nucleic acid may be a chromosome (complex nucleic acid) and the micro-particle may have discrete dielectric properties eg is metallic (gold) etc. This is particularly useful for the separation of human (and other species) chromosomes where different chromosomes may have similar sizes, and dielectric properties. Technologies such as flow cytometry are currently used to sort chromosomes on a size basis, and are thus incapable of discriminating chromosomes of similar sizes. In the case of humans, chromosomes 9–12 inclusive can not readily be separated by flow cytometry due to their similar size. According to our approach if these chromosomes are pre-labelled with a 'dielectric' marker they can be separated on the basis of their dielectric properties.

In practice this is achieved by partially denaturing the chromosomal DNA (by for example heat, chemical treatment, or electrical treatment), and subsequently hybridising a complementary (to a defined nucleic acid sequence) nucleic acid probe. The nucleic acid probe may preferably consist of at least 15 nucleotides, and may itself be pre-labelled with an entity which has an affinity for a binding agent. For example, but not exclusively, the label may be 'biotin' which can be incorporated into a nucleotide, or added to the terminal region of the probe sequence. The binding agent may be for example, an antibody which has specificity for the label, or alternatively a protein/enzyme etc which has an affinity for the label of choice. The binding agent may in turn be bound to a micro-particle which could as both a dielectric amplifier (by amplifying additional dielectric properties) and/or an aid to detection of the chromosomes of choice. Thus a complex could be envisaged as described in FIG. 9. Following the 'dielectric labelling' of the ligand chromosome it can then be separated from the other chromosomes on the basis of different dielectric properties. Practically this may be achieved by using different migration frequencies, or selective electrode arrays—see FIGS. 1 to 3.

Thus it is possible to see that the selective separation and identification of chromosomes could be achieved using the method described above. This has practical application in clinical diagnostics where, identification and characterisation of chromosome alterations, eg re-arrangements/dilutions, insertion of foreign DNA eg viral DNA is important.

Alternatively, the chromosome may be the particle and it may be treated by hybridisation thereto of a nucleic acid probe bearing a label (the ligand) which alters the TWFM characteristics of the chromosome and optimally which also aids its detection, eg a fluorescent marker.

in order to observe TWFM for an altered particle which is distinct from the behaviour of the unaltered particle under identical conditions, one needs to select the conditions with care. It has been established that in order for TWFM to occur, the particles need to be repelled from the electrodes so as to be levitated above the electrodes and not drawn down onto the electrodes. Simultaneously, the particles need to be propelled along the electrode array by the electric field travelling wave. The dielectrophoresis force responsible for the repulsion or attraction of the particles to the electrodes is determined by the real component of the induced dipole moment in the particle. The propulsion of the particle along the electrode array is determined by the magnitude of the imaginary component of the induced dipole moment and the direction of movement by its sign. Both of these real and imaginary components vary with field frequency and depend also on the nature of the particle and the suspending medium. To produce a visible difference in behaviour between the altered and unaltered particles one needs to find field conditions and suspending medium characteristics in which the relationship between the real and imaginary components of the dipole moment are adequately different for the two forms of the particle. This can be done as follows.

Figures 13A, 13B:
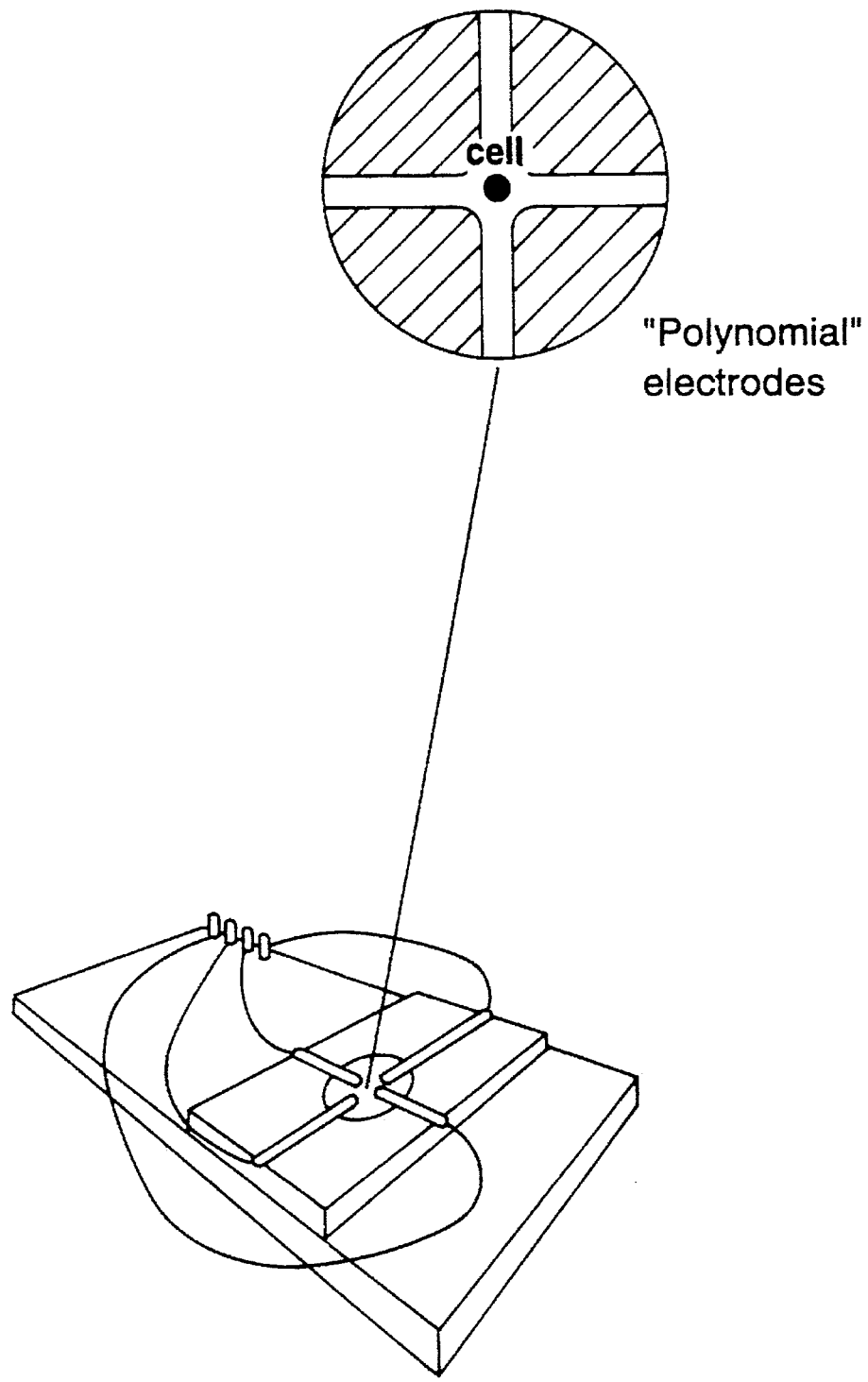
FIG. 13 shows an electrode array useful in determining frequencies and suspending media likely to produce satisfactory TWFM characteristics for a particle.

Particles for which characteristics are to be determined are suspended in a chosen medium and are pipetted into a chamber having at its base an array of electrodes as shown in FIG. 13. A rotating electric field is applied to the electrode array and the frequency of the rotating field is scanned stepwise over a desired range, eg. from 10 to $10^{10}$ Hz. At each frequency the angular velocity and sense of the electrorotation produced in the particles is noted as a measure of the imaginary component of the induced dipole moment. This is plotted as the line TRANS in FIG. 14. The line DEP representing the dielectrophoretic force experienced by the particles can either be computed from the line TRANS taking into account the complex polarisability of the particles or experimentally determined in the same apparatus. For the latter, the electrodes are subjected to a field such that adjacent electrodes have a sinusoidal voltage phased 180° appart. The speed at which the particles move away from the central area between the electrodes (positive DEP effect) or move towards the central area (negative DEP effect) is plotted against frequency.

Figure 14:
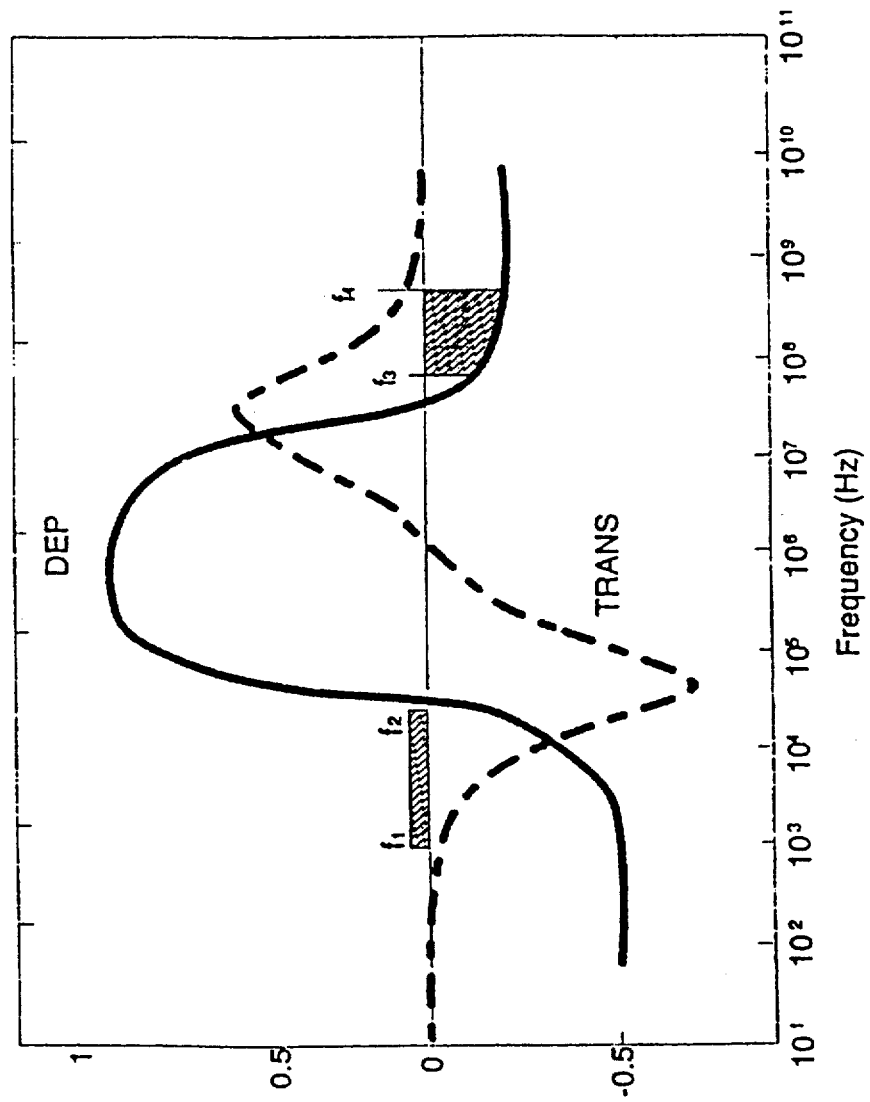
FIG. 14 shows graphs illustrating the dielectric properties of live cells in a medium of conductivity of $5 \times 10^{-4}$ $5m^{-1}$.

A typical result for a live cell such as an erythrocyte or yeast cell is seen in FIG. 14. The shape of curve is typical of live cells, the frequencies will vary with cell type. TWFM will be seen in the two areas $f_1$–$f_2$ and $f_3$–$f_4$ where the dielectrophoresis (DEP) is negative so that the particles are repelled up from the electrodes, and the interaction with the travelling wave produces a net force along the electrode array (non-zero TRANS). The direction in which the particles move depends on whether TRANS is positive or negative.

Figure 15:
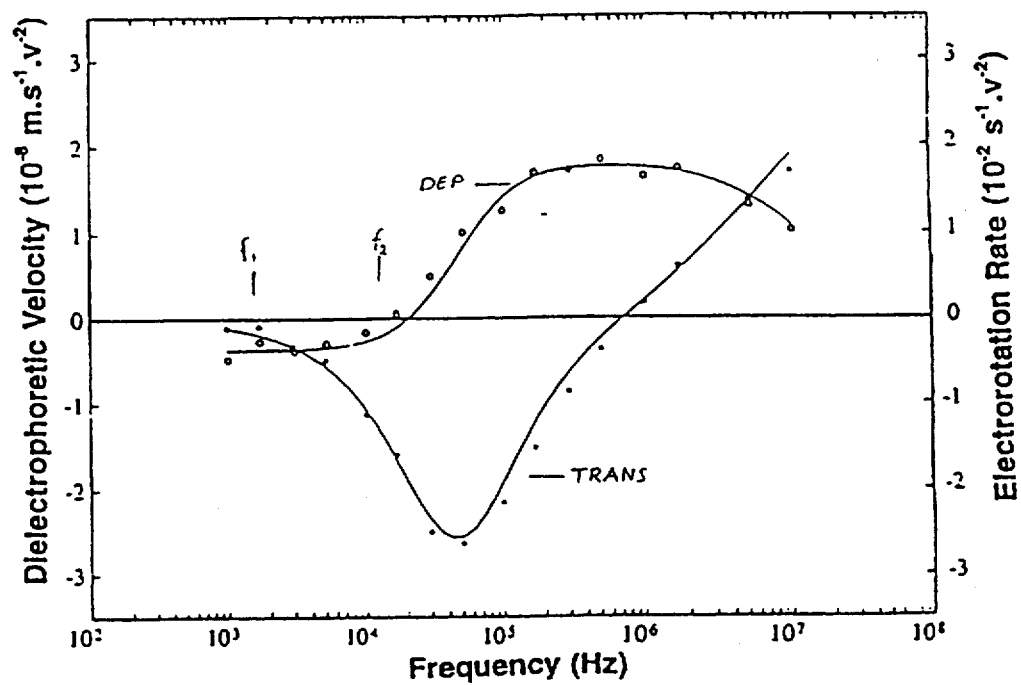
FIG. 15 shows graphs illustrating the dielectric properties of live yeast cells.
Figure 16:
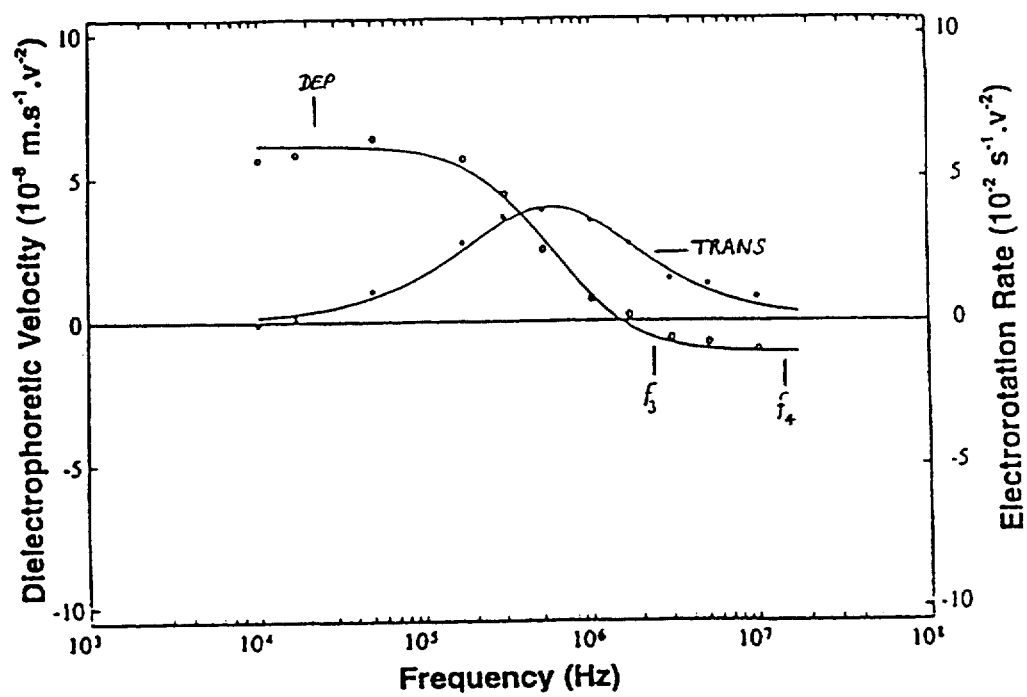
FIG. 16 shows graphs illustrating the dielectric properties of dead yeast cells in a similar medium.

Actual curves for live and killed yeast cells are shown in FIGS. 15 and 16. It can be seen that the TWFM region between $f_1$ and $f_2$ is present only for live cells. Accordingly, the killed (i.e. altered) cells will remain stationary whilst the original cells will migrate under these frequency conditions.

The conductivity of the suspending medium will affect the shape of the curves plotted as in FIGS. 14 to 16. The conductivity may be adjusted empirically to obtain suitably shaped curves.

The frequency range illustrated will often be found most convenient but there may be other TWFM areas beyond this range in one or both directions that may be employed.

EXAMPLE 1

Selective Manipulation and Separation of Untreated and Heat-treated Yeast Cells.

Baker's yeast cells (*Saccharomyces cerevisiae*, strain RXII, obtained from the Department of Biophysics, Free University, Berlin) were grown at 30° C. in an aqueous medium consisting of sucrose (50 g/l), yeast extract (5 g/l) and peptone (5 g/l). Growth curves for the yeast culture were obtained by measuring the change in optical absorbance of the yeast suspension during its batch culture using a double beam spectrophotometer. When the cells had reached the stationary phase of growth, they were harvested and washed four times in 280 mM mannitol. The cells were rendered non-viable by heating to 90° C. in a waterbath for 20 minutes, after which they were washed as before in 280 mannitol.

Cell viability was determined using a methylene blue stain. The stain was prepared from three stock solutions comprising: [1] Methylene blue (0.250 g/l) in 20 ml of distilled water, [2] $KH_2PO_4$ (2.722 g) in 100 ml of distilled water, [3] $Na_2HPO_4$ (0.248 g) in 10 ml of distilled water. A working solution was prepared by mixing 2 ml of [1], 99.7 ml of [2] and 0.25 ml of [3]. No less than 0.02 ml yeast of suspension was mixed with 0.8 ml suspension medium plus 0.08 ml of methylene blue. Non-viable cells took up the blue dye into the cytoplasm and could be differentiated from the live cells, which excluded the dye from their interiors. Suspensions with different relative amounts of viable and non-viable cells were made by mixing, were made in 280 mM mannitol having electrical conductivities (adjusted by adding NaCl) of 1, 10 and 50 mS/m as determined at 50 kHz using platinum black electrodes and a HP 4192A impedance analyser.

50 microliter samples of such suspensions were pipetted on to a microelectrode array of the same form of FIG. 1, fabricated using standard photolithography and of geometry and electrical connections as described by Huang, Wang, Tame and Pethig in their paper "Electrokinetic behaviour of colloidal particles in travelling electric fields: studies using yeast cells" J. Phys. D:Appl. Phys. 26 (1993) 1528–1535, so as to subject the cells to the forces exerted by travelling electric fields. The electrode widths were of nominal dimension 14 microns, the gap between adjacent electrodes was of the order 6 microns, and the distance across the channel between opposing electrode taps was 30 microns. The voltage phase relationships were as shown in FIG. 1, so that the effective periodic length $\lambda$ of the travelling field was 80 microns. These dimensions were chosen to provide the most selective TWFM effects for particles such as yeast cells which have an average diameter of the order 6 to 8 microns. The travelling electric fields were established by sequentially addressing the electrodes with sinusoidal voltages of phase separation as shown in FIG. 1, and the amplitude of the applied voltages was 5 V (peak-peak). A cover slip was placed over the suspension and the resulting motions of the cells were viewed through a microscope.

On examining the TWFM of the viable yeast cells at a suspending medium conductivity of 1 mS/m the viable cells did not exhibit TWFM at all the frequencies investigated between 1 kHz and 10 MHz, and remained trapped at the electrode edges and tips. For a medium conductivity of 10 mS/m the viable cells exhibited TWFM in the frequency range between 8 kHz and 60 kHz and in so doing moved along the channel between the electrode tips in a direction opposing that of the imposed travelling field. For a medium conductivity of 50 mS/m, the viable cells exhibited TWFM between 3 kHz and 300 kHz, again moving along the channel in the opposite sense to that of the imposed travelling field. The behaviour of the non-viable cells, identified by their blue staining, was however significantly different. For a suspending medium conductivity of 1 mS/m, the non-viable cells remained trapped at the electrodes at all frequencies from 1 kHz to 2 MHz, but between 3 MHz and 10 MHz they exhibited TWFM and moved along the channel in the same direction as the travelling field. Thus, for a medium conductivity of 1 mS/m, the non-viable cells could be selectively removed from the viable cells in the cell mixture, by applying a travelling field of frequency 3 MHz. For a medium conductivity of 10 mS/m, the non-viable cells exhibited TWFM only for frequencies above 3 MHz, and in so doing travelled along the channel in a direction opposing that of the travelling field. Thus, at 10 mS/m conductivity of the suspending medium, by applying a signal frequency of 30 kHz, the viable cells were selectively moved down the channel in a direction opposing the travelling field, whilst for a frequency of 5 MHz the non-viable cells were selectively move along the channel in the same direction as the travelling field. By applying a 30 kHz travelling field to the electrodes at the same time and in the same direction as a 5 MHz travelling field, evidence was obtained for the possibility of moving both the viable and non-viable cells down the channel and over the electrodes at the same time and in opposite directions so as to facilitate their complete separation from each other. At a medium conductivity of 50 mS/m, the non-viable yeast cells exhibited a relatively weak TWFM in the frequency range between 70 kHz and 700 kHz, and they travelled along the channel in the opposite direction to that of the travelling field. Thus at a medium conductivity of 50 mS/m, by applying a travelling field frequency of 50 kHz, the non-viable cells remained trapped at the electrodes, whilst the viable ones travelled down the channel in a direction opposing that of the travelling field. By superimposing another travelling field at 500 kHz and in the opposite direction to that of the 50 kHz travelling field, an indication of the non-viable cells moving in the opposite direction to that of the viable cells was observed, but this separation effect was not as large as that observed for a medium conductivity of 10 mS$^{-1}$m for superimposed fields of 30 kHz and 5 MHz.

These results demonstrate the capability of selectively identifying and separating "treated" particles from "non-treated" particles, and provide guidance in the principles involved in choosing the most effective conductivity of the suspending medium (liquid or gel) and of the frequency or frequencies, and direction, of the applied travelling field or fields.

Further examples of analyses and separations possible using the techniques of the invention are as follows.

A double stranded DNA molecule having attached to it a protein such as a transcription factor (altered particle) may be separated from DNA lacking the protein by selecting conditions under which only the altered particle migrates and the protein may then be cleaved off isolated, sequenced and studied.

In a variant of the above the protein-DNA complex may be separated from similar protein-DNA complexes to which an additional protein has bound (altered particle).

A cell having on its surface a receptor for a ligand such as an antibody, growth factor, neurotransmitter or other biochemical messenger may be separated from similar cells to which the appropriate ligand has bound.

Cells which have been successfully transfected such that they express a new gene product, possibly located in the cell membrane, may be differentiated from the original form of cell.

Cells to which a phage has bound may be differentiated from non-infected cells.

Cells may have an oligonucleotide probe bound to a label such as a gold particle introduced into them to bind to complementary genomic DNA during cell division to separate dividing from non-dividing cells.

Methods of detection used are not limited to microscopy. For instance, where the altered particle includes a dye or fluorescent marker, the presence of altered particles may be monitored by an appropriate spectrophotometer.

The electrodes need not be arranged as a linear "ladder". Instead the "ladder" of electrodes may be curved or otherwise non-linear. It may form a spiral or serpentine path or may be a closed path around which the particles travel.

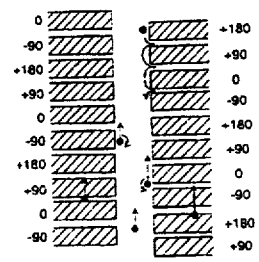

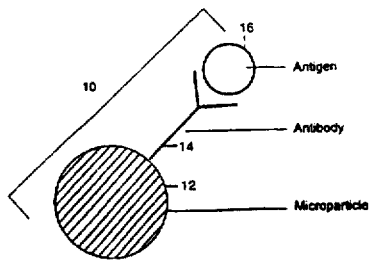

We claim:

1. A method of analysis or separation comprising:
   treating a plurality of original, particles to form a subplurality of altered particles from at least some of said plurality of original particles, said subplurality of altered particles having travelling wave field migration properties distinct from those of said plurality of original particles; and
   producing translatory movement of said subplurality of altered particles and/or said plurality of original particles by travelling wave field migration using conditions such that said translatory movement of said subplurality of altered particle differs from said translatory movement of said plurality of original particles under the same conditions.

2. A method as claimed in claim 1, wherein:
   said subplurality of altered particles are observable by use of a light-microscope.

3. A method as claimed in claim 1, wherein:
   said subplurality of altered particles are too small to be observed by use of a light-microscope.

4. A method as claimed in any of claims 1, 2 or 3, wherein said subplurality of altered particles are formed from said plurality of original particles by a treatment comprising:
   forming respective complexes between said subplurality of altered particles and a ligand.

5. A method as claimed in claim 4, wherein said respective complexes comprise:
   a first linking moiety connecting said subplurality of altered particles and said ligand.

6. A method as claimed in claim 5, wherein said respective complexes further comprise:
   a label connected to said ligand.

7. A method as claimed in claim 6, wherein:
   said label is connected to said ligand via a second linking moiety.

8. A method as claimed in claim 1, wherein:
   said plurality of original particles are treated so as to form said subplurality of altered particles by forming respective complexes between respective ones of said plurality of original particles and a ligand, said complexes having a dielectric property different from a dielectric property of said plurality of original particles, and said complexes are subjected to said travelling wave field migration with respect to a plurality of electrodes under conditions which displace said complexes away from said plurality of electrodes in a direction perpendicular to a direction of said travelling wave field migration and which produce migration dependent on an imaginary component of an induced dipole moment of said complexes.

9. A method as claimed in any one of claims 1 to 3, wherein:
   said subplurality of altered particles are formed by a treatment which alters an intrinsic dielectric property of said plurality of original particles.

10. A method as claimed in any one of claim 1, 2, 3 or 8, wherein:
    an effective wavelength of a travelling field is from 8 to 12 times a respective size of said subplurality of altered particles as measured transverse to a direction of movement under said travelling wave field migration.

11. A method as claimed in claim 5, wherein:
    said first linking moiety is an immunological binding partner for said ligand carried by said particle or an oligonucleotide carried by said particle, said first linking moiety including a nucleotide sequence hybridizing with a nucleotide sequence present in said ligand.

12. A method as claimed in claim 7, wherein:
    said second linking moiety is an immunological binding partner for said ligand carried by said label or an oligonucleotide carried by said label, said second linking moiety including a nucleotide sequence hybridizing with a nucleotide sequence present in said ligand.

13. A method of analysis or separation comprising:
    treating a plurality of original particles to form a subplurality of altered particles from only some of said plurality of original particles, said subplurality of altered particles having travelling wave field migration properties distinct from travelling wave field migration properties of said plurality of original particles;
    subjecting said plurality of original particles and said subplurality of altered particles to a row of parallel electrodes; and
    producing translatory movement of said subplurality of altered particles and/or said plurality of original particles by travelling wave field migration by applying a travelling wave having a wavelength of about 8 to 12 times the size of said subplurality of altered particles and/or said plurality of original particles, to said row of parallel electrodes;

whereby said translatory movement of said subplurality of altered particles differs from said translatory movement of said plurality of original particles.

14. A method of analysis or separation comprising:

treating a plurality of original particles to form a subplurality of altered particles from only some of said plurality of original particles, said subplurality of altered particles having travelling wave field migration properties distinct from travelling wave field migration properties of said plurality of original particles;

subjecting said plurality of original particles and said subplurality of altered particles to a row of parallel electrodes; and producing translatory movement of said subplurality of altered particles and/or said plurality of original particles by travelling wave field migration;

whereby said translatory movement of said subplurality of altered particles differs from said translatory movement of said plurality of original particles.

* * * * *

UNITED STATES PATENT AND TRADEMARK OFFICE
CERTIFICATE OF CORRECTION

PATENT   : 5,653,859

DATED    : August 5, 1997

INVENTOR(S) : Parton et al

It is certified that error appears in the above-identified patent and that said Letters Patent is hereby corrected as shown below:

The title page showing the number of claims and drawing sheets should be deleted and substitute therefore the attached title page.

In the drawings, sheets 10 of 12, 11 of 12 and 12 of 12, showing Figs. 14, 15 and 16, have been added, as shown of the attached pages.

Signed and Sealed this

Twenty-fifth Day of May, 1999

Attest:

Q. TODD DICKINSON

*Attesting Officer*    *Acting Commissioner of Patents and Trademarks*

United States Patent [19]

Parton et al.

[11] Patent Number: 5,653,859
[45] Date of Patent: Aug. 5, 1997

[54] METHODS OF ANALYSIS/SEPARATION

[76] Inventors: Adrian Parton, 6 Swan Grove, Exning, Suffolk CB8 7HX, United Kingdom; Ying Huang; Xiao-Bo Wang, both of P.O. Box 89, Houston, Tex. 77030; Ronald Pethig, Lleyn, Telford Road, Mania Bridge, Gwynedd LL59 5DT, United Kingdom; Alastair R. MacGregor, Field House, Thriplow Road, Fowlmere, Royston, Hertfordshire SG8 7OT, United Kingdom; Denise V. Pollard-Knight, 20 Highfield Hall, Highfield Lane, St. Albans AL4 ORL, United Kingdom

[21] Appl. No.: 495,447

[22] PCT Filed: Jan. 21, 1994

[86] PCT No.: PCT/GB94/00121

§ 371 Date: Nov. 20, 1995

§ 102(e) Date: Nov. 20, 1995

[87] PCT Pub. No.: WO94/16821

PCT Pub. Date: Aug. 4, 1994

[30] Foreign Application Priority Data

Jan. 21, 1993 [GB] United Kingdom ............... 9301122

[51] Int. Cl.[6] .................... G01N 27/26; G01N 27/447
[52] U.S. Cl. ................................ 204/450; 204/600
[58] Field of Search .......................... 204/600, 450, 204/451, 452, 453, 454, 455, 602, 601, 603, 604, 605

[56] References Cited

U.S. PATENT DOCUMENTS

| | | | |
|---|---|---|---|
| 4,390,403 | 6/1983 | Batchelder | 204/457 |
| 4,900,414 | 2/1990 | Sibalis | 204/457 |
| 5,108,568 | 4/1992 | Van Alstine | 204/450 |
| 5,228,960 | 7/1993 | Liu et al. | 204/451 |
| 5,284,558 | 2/1994 | Linhardt et al. | 204/451 |
| 5,431,793 | 7/1995 | Wang et al. | 204/452 |

FOREIGN PATENT DOCUMENTS

| | | |
|---|---|---|
| 519250 | 12/1992 | European Pat. Off. |
| 412745 | 2/1993 | Germany |
| 92/07657 | 5/1992 | WIPO |
| WO93/04199 | 3/1993 | WIPO |

OTHER PUBLICATIONS

Senichi Masuda et al., "Separation of Small Particles in Liquid by Nonuniform Traveling Field", IEEE Transactions on Industry Appln. vol. A–23 No. 3 (May/Jun. 1987) 424–480.

Rolf Hagedorn et al. "Traveling–Wave Dielectrophoresis of Microparticles," Electrophoresis 1992 vol. 13 (1992) 49–54 No Month Available.

Masao Wastlizu, "Electrostatic Manipulation of Biological Objects", Journal of Electrostatics vol. 25, No. 1 (Jun. 1990) 109–123.

(List continued on next page.)

*Primary Examiner*—Kathryn L. Gorgos
*Assistant Examiner*—John S. Starsiak, Jr.
*Attorney, Agent, or Firm*—Cushman, Darby & Cushman IP Group of Pillsbury Madison & Sutro LLP

[57] ABSTRACT

Particles are subjected to travelling wave field migration (TWFM) to migrate the particles over an array of microelectrodes. Altered particles are produced by treating original particles in such a way so as to alter their TWFM characteristics and the altered TWFM characteristics are employed for analysis and/or separation of the altered particles. The particles may be cells, bacteria, viruses, biomolecules or plastics microspheres. They may be altered by binding to a ligand such as a metal microparticle via a selective linking moiety such as an antibody/antigen or oligonucleic acid, or be physical or chemical treatments.

14 Claims, 12 Drawing Sheets